United States Patent [19]

Hastings et al.

[11] 4,278,761

[45] Jul. 14, 1981

[54] ENZYME ASSAY AND KIT THEREFOR

[75] Inventors: John W. Hastings, Constance, Fed. Rep. of Germany; Shiao-Chun Tu, Houston, Tex.

[73] Assignee: President and Fellows of Harvard College, Cambridge, Mass.

[21] Appl. No.: 107,439

[22] Filed: Dec. 26, 1979

[51] Int. Cl.³ .................. C12Q 1/6; C12N 11/18; C12N 11/14; C12N 11/02

[52] U.S. Cl. .................. 435/8; 435/14; 435/15; 435/18; 435/21; 435/175; 435/176; 435/177; 435/178; 435/179; 435/180; 435/181; 435/182

[58] Field of Search .................. 435/8, 14, 15, 18, 21, 435/175, 176, 177, 178, 179, 180, 181, 182

[56] References Cited

PUBLICATIONS

Jablonski et al., Proc. Natl. Acad. Sci., vol. 73, pp. 3848–3851, 1976.

Mosbach et al., Methods In Enzymology, ed. Mosbach, vol. 44, pp. 453–478, Academic Press, 1976.

Oskar Zaborsky, Immobilized Enzymes, pp. 124–126, Chemical Rubber Company Press, 1973.

Lemuel B. Wingard, Jr. et al., Applied Biochemistry and Bioengineering, vol. 1, Immobilized Enzyme Principles, pp. 204–211, 1976.

Ichiro Chibata, Editor, Immobilized Enzymes, pp. 218–219, A Halstead Press Book, John Wiley & Sons, 1978.

*Primary Examiner*—Robert J. Warden

[57] ABSTRACT

Compositions and methods featuring, in one aspect, an enzyme assay in which one of a pair of enzymes is immobilized on an insoluble support, and brought into contact with a solution containing the other enzyme of the pair and the substrates of both enzymes. The enzymes catalyze reactions between the substrates, and one or more products of the last such reaction are measured.

7 Claims, 1 Drawing Figure

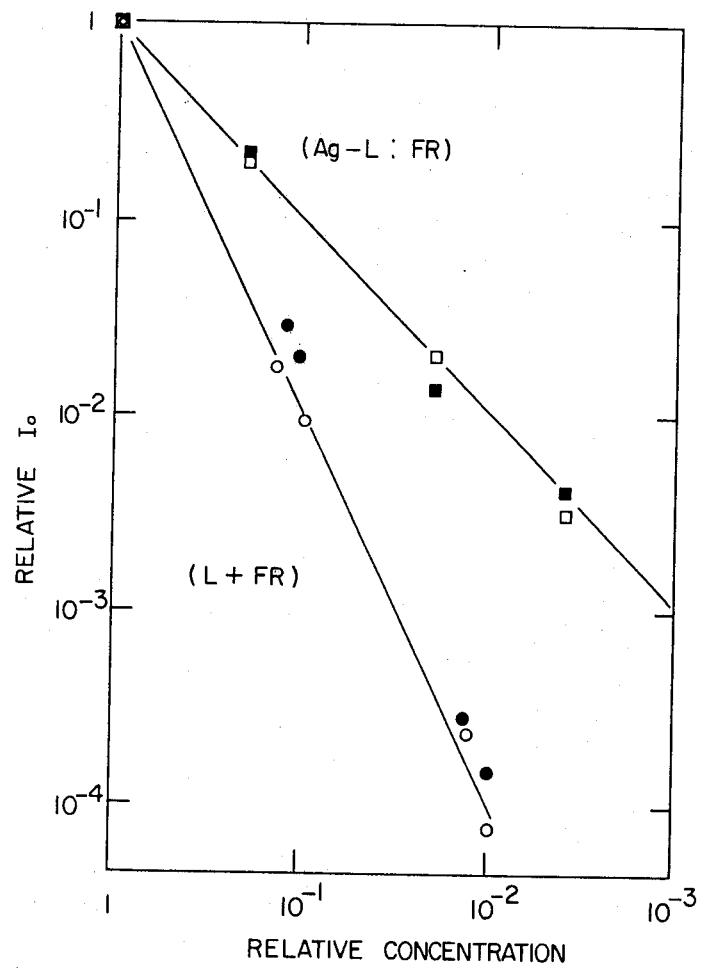

ENZYME ASSAY AND KIT THEREFOR

The invention described herein was made in part in the course of work under a postdoctoral fellowship from the National Institute of Health.

This invention relates to an assay for enzymes and enzyme substrates wherein an immobilized enzyme is contacted with a solution containing a second enzyme and substrates of both enzymes, and a reaction product is measured.

In two-enzyme systems in which a reaction product of the first enzyme and its substrates serves as a substrate for the second enzyme, it is often desirable to assay one of the enzymes or substrates. By "substrate" is meant any compound which reacts with either enzyme. A problem with conventional assays in such two-enzyme systems is that in many cases a product of the first reaction is degraded or otherwise lost before the second enzyme can act on it. This problem is demonstrated in the flavin reductase, bacterial luciferase system, in which flavin reductase acts on flavin mononucleotide (FMN) and NADH or NADPH to produce $FMNH_2$, which in turn is acted upon by luciferase in the presence of oxygen (and in some cases an aldehyde) to produce light. These reactions are summarized by the following equations:

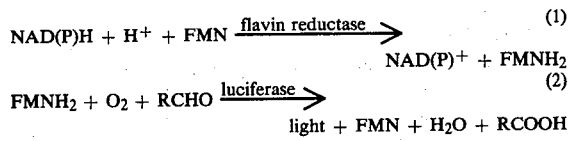

$$NAD(P)H + H^+ + FMN \xrightarrow{\text{flavin reductase}} NAD(P)^+ + FMNH_2 \quad (1)$$

$$FMNH_2 + O_2 + RCHO \xrightarrow{\text{luciferase}} \text{light} + FMN + H_2O + RCOOH \quad (2)$$

In vitro studies of luciferase and flavin reductase in solution by Gibson et al. (1966) in *Flavins and Flavoproteins*, ed. Slater, pp. 341–359 and by Hastings et al. (1977), *Ann. Rev. Microbiol.* 31, 549–595 have shown that the product of the first reaction, $FMNH_2$, tends to autoxidize back to FMN before it can be acted upon by luciferase. This finding is consistent with Hastings et al. (1965) *J. Biol. Chem.* 240, 1473–1481, which showed that the activity, as measured by light emission, of luciferase in solution with flavin reductase decreased by a factor of 100 when the solution was diluted by a factor of 10, before initiation of the reaction with FMN and NADH or NADPH.

Duane et al. (1975) *Mol. and Cell Biochem.* 6, 53–64 have suggested that, in vivo, flavin reductase and luciferase may form a complex, and Ne'eman et al. (1977) *J. Biol. Chem.* 252, 5154 have suggested that luciferase functions in vivo in association with membrane proteins.

Other workers have recognized that, in two-enzyme systems, the efficiency of the second reaction can be enhanced when the first reaction product is produced in the vicinity of the enzyme which is to act on it. The approach which has been employed to facilitate reactions in this way has been to immobilize both enzymes on a single support particle. Methods using this approach are described in Jablonski et al. (1976) *Proc. Natl. Acad. Sci.* 73, 3848–3851 and Mosbach et al. (1976) in *Methods in Enzymology*, ed. Mosbach (Academic Press, NY) 44, pp. 453–478.

We have now found an assay method for enzyme and enzyme substrates in which the bonding of one enzyme of a pair to an insoluble support unexpectedly enables the other enzyme of the pair to bind to it. This binding prevents a product of the first enzymatic reaction, which product serves as a substrate for the second reaction, from being lost before the second enzyme can act on it. Thus, reactants behave in a stoichiometrically predictable way at all concentrations, and the quantity of an unknown enzyme or substrate is directly proportional to the measurable products of the second enzymatic reaction.

The method of the invention has a large number of applications, one of the most important being the measurement of compounds associated with disease states or genetic abnormalities. For example, the luciferase-flavin reductase system can be used to assay for NADH, a compound useful to measure in numerous clinical situations. For example, heart attacks can be diagnosed by using the method to detect the elevated blood NADH level produced by the reaction of characteristically large amounts of lactate dehydrogenase with lactic acid. Other applications of the invention include research laboratory assays for compounds of scientific interest such as luciferase.

Accordingly, this invention provides compositions and methods for assaying either enzyme, or any of the substrates of either enzyme, for enzyme pairs in which a product of the first enzymatic reaction serves as one of the substrates for the second enzyme of the pair. The method comprises immobilizing one of the enzymes of the pair by bonding it, by conventional protein immobilization techniques, to an insoluble support such as agarose, binding the other enzyme to the bound enzyme, bringing into contact with the bound enzymes substrates of both enzymes, and measuring at least one of the final products of the second enzymatic reaction by conventional procedures or apparatus. The binding of the other enzyme to the immobilized enzyme can be conveniently combined with the step of bringing a product of the immobilized enzyme into contact with and serving as a substrate for the second enzyme by carrying out both steps at once in one solution.

The enzyme pairs to which the invention can be applied include the bacterial luciferase-flavin reductase enzyme pair, and glycolytic enzyme pairs. By "glycolytic enzyme pairs" is meant those pairs of glycolytic enzymes in which one enzyme catalyzes a reaction, a product of which is a substrate for the second enzyme of the pair; such enzymes, like luciferase and flavin reductase, have little or no tendency to complex or bind to each other in solution. Glycolytic enzyme pairs and the reactions they catalyze are listed in Table I below.

For each pair of reactions in Table I, the first listed enzyme catalyzes the first listed reaction, which produces a substrate for the second listed enzyme. For each pair of reactions, one final product of the second reaction is measured or assayed to determine the amount of either enzyme of the enzyme pair or the amount of any one of the substrates taking part in either of the pair of reactions. For example, referring to the first enzyme pair of Table I, the method of the invention can be used to assay hexokinase, or phosphoglucose isomerase, or glucose or ATP. Either hexokinase or phosphoglucose isomerase is covalently bonded to an insoluble support, the other enzyme is bound to the immobilized enzyme, glucose and ATP are added, and fructose 6-phosphate is measured using standard techniques. The amount of fructose 6-phosphate is directly proportional to the amount of the compound being assayed. The compounds assayed and the assay method for the other eight enzyme pairs of Table I are analogous to those described above for hexokinase and phosphoglucose isomerase. In each case, the amount of one of the final products of the second reaction is measured by any conventional procedure.

of standards containing known amounts or concentrations of the compound being assayed.

The kit may also contain, as optional additional components, supplies of other compounds such as oxidizing agents, buffers, and any of the desired or necessary

TABLE I

| | Enzyme pair | Reactions |
|---|---|---|
| 1. | Hexokinase | Glucose + ATP → glucose 6-phosphate + ADP + H$^+$ |
| | Phosphoglucose isomerase | Glucose 6-phosphate → fructose 6-phosphate |
| 2. | Phosphoglucose isomerase | Glucose 6-phosphate → fructose 6-phosphate |
| | Phosphofructokinase | Fructose 6-phosphate + ATP → fructose 1,6-diphosphate + ADP + H$^+$ |
| 3. | Phosphofructokinase | Fructose 6-phosphate + ATP → fructose 1,6-diphosphate + ADP + H$^+$ |
| | Aldolase | Fructose 1,6-diphosphate $\rightleftarrows$ dihydroxyacetone phosphate + glyceraldehyde 3-phosphate |
| 4. | Aldolase | Fructose 1,6-diphsophate $\rightleftarrows$ dihdroxyacetone phosphate + glyceraldehyde 3-phosphate |
| | Triose phosphate isomerase | Dihydroxyacetone phosphate $\rightleftarrows$ glyceraldehyde 3-phosphate |
| 5. | Triose phosphate isomerase | Dihydroxyacetone phosphate $\rightleftarrows$ glyceraldehyde 3-phosphate |
| | Glyceraldehyde 3-phosphate dehydrogenase | Glyceraldehyde 3-phosphate + P$_i$ + NAD$^+$ $\rightleftarrows$ 1,3-diphosphoglycerate + NADH + H$^+$ |
| 6. | Glyceraldehyde 3-phosphate dehydrogenase | Glyceraldehyde 3-phosphate + P$_i$ + NAD$^+$ $\rightleftarrows$ 1,3-diphosphoghlycerate + NADH + H$^+$ |
| | Phosphoglycerate kinase | 1,3-Diphosphoglycerate + ADP $\rightleftarrows$ 3-phosphoglycerate + ATP |
| 7. | Phosphoglycerate kinase | 1,3-Diphosphoglycerate + ADP $\rightleftarrows$ 3-phosphoglycerate + ATP |
| | Phosphoglyceromutase | 3-Phosphoglycerate $\rightleftarrows$ 2-phosphoglycerate |
| 8. | Phosphoglyceromutase | 3-Phosphoglycerate $\rightleftarrows$ 2-phosphoglycerate |
| | Enolase | 2-Phosphoglycerate $\rightleftarrows$ phosphoenolpyruvate + H$_2$O |
| 9. | Enolase | 2-Phosphoglycerate $\rightleftarrows$ phosphoenolpyruvate + H$_2$O |
| | Pyruvate kinase | Phosphoenclpyruvate + ADP + H$^+$ → pyruvate + ATP |

The compounds assayed and the assay method for the luciferase-flavin reductase enzyme pair are analogous to those described above for glycolytic enzyme pairs. Thus, to assay flavin reductase, luciferase, FMN, O$_2$, NADH or NADPH, and the aldehyde (RCHO) being used, luminescence is measured by standard techniques, and is directly proportional to the amount of the compound being assayed.

For any of the enzyme pairs used in accordance with the invention, the reactants other than the unknown enzyme or substrate are maintained in excess over the stoichiometric amount required to react with all of the amount of the unknown to be assayed, so that the reaction is limited by the amount of that reactant.

The supports which can be used in accordance with the invention include insoluble supports such as cellulose, agarose, dextran or cross-linked polyvinyl alcohol or polyacrylamide.

In a two-enzyme system in which a reaction product of a first enzyme with first substrates serves as one of the substrates of a second enzyme, a suitable kit for assaying one of the enzymes or substrates, except the reaction product substrate, includes as components: (1) a supply of one of the enzymes immobilized on an insoluble support; (2) a supply of the other enzyme and substrates of the system, except for the enzyme or substrate to be assayed; and (3) a supply of standards containing known amounts or concentrations of the enzyme or substrate to be assayed.

A suitable kit for assaying one of the enzymes or substrates of a glycolytic enzyme pair or of the luciferase-flavin reductase enzyme pair includes as components: (1) a supply of one of the enzymes of the enzyme pair which has been immobilized by being covalently bonded to an insoluble support; (2) a supply of the other enzyme; this enzyme may be supplied separately, or it may be supplied already bound to the support-bonded enzyme; (3) a supply of the substrates, not being assayed, necessary for the two reactions; and (4) a supply facilities for carrying out the tests.

In the drawing is a graph of the relation between enzyme concentration and initial maximum luminescence intensity in soluble and bound luciferase-flavin reductase systems.

The following specific example is intended to illustrate more fully the nature of the present invention without acting as a limitation upon its scope.

EXAMPLE

This example describes the immobilization of luciferase, the binding of flavin reductase to it, and the evidence showing the proportional relationship between dilution and reaction rate.

Luciferase and flavin reductase were purified from *Beneckea harveyi* strain 391 by the method described in Gunsalus-Miguel et al. (1972) *J. Biol. Chem.* 247, 398–404. Luciferase was purified to a specific activity of $1.7 \times 10^{14}$ q/s/mg, as determined at 23° by a standard assay in which 1 ml of $5 \times 10^{-5}$ M FMNH$_2$ (catalytically reduced) was injected into 1 ml 0.05 M phosphate, pH 7, containing 0.2% bovine serum albumin (BSA), 0.001% decanal, and the luciferase sample. The measure of activity, initial maximum light intensity (Io), was measured at 23° C. with a calibrated photometer by the method of Mitchell et al. (1971) *Anal. Biochem.* 39, 243–250. An NADH-dependent flavin reductase activity was resolved from luciferase activity at the stage of DEAE-Sephadex column chromatography. The peak flavin reductase activity fractions were combined to provide a partially purified flavin reductase which exhibited an activity of 0.21 units/mg. One unit was defined as the oxidation of 1 μmole NADH at 23° C. in 1 ml. 0.05 M phosphate, pH 7, $5 \times 10^{-5}$ M FMN, and $2 \times 10^{-4}$ M NADH.

Luciferase of known activity was immobilized on agarose gel beads using the method of cyanogen bromide activation described in Porath et al. (1976) in *Methods in Enzymology*, ed. Mosbach (Academic Press, NY) Vol. 44, pp. 19–45. Agarose gel beads, about 5 ml bed volume, were washed by filtration with 200 ml of water and suspended with constant stirring in an equal volume of water; 1.25 g of cyanogen bromide were added over a period of 20 to 30 min. During this step, the temperature was kept between 18° C. and 22° C. by the addition of ice and the pH kept at 10.5 to 11.5 by the addition of 2.5 N NaOH. The activation of gel was considered about complete when no more base addition was needed to maintain the desired pH. The suspension was immediately cooled to 4° C., filtered, washed with 200 ml of precooled 0.1 M phosphate, pH 7.5, and suspended in 5 ml of the same precooled buffer containing 10 mg of luciferase. After gentle shaking at 4° C. for about 18 hrs., the suspension was washed by centrifugation at 0° C. five times in 10 ml of 0.1 M phosphate, pH 7. After each centrifugation, the supernatant was collected for determination of luciferase activity and protein context, by the method described in Lowrey et al., (1951) *J. Biol. Chem.* 193, 265–275. This permitted the calculation, by difference, of the amount of bound luciferase; this value was used in determining the specific activity of the immobilized luciferase. The thoroughly washed gel containing immobilized luciferase was then suspended in an equal volume of 0.1 M phosphate, pH 7, 0.1 mM dithiothreitol and stored at 0° C.

Partially purified flavin reductase was bound to the gel-bonded luciferase by mixing the two for five minutes at 0° C. in 0.05 M phosphate, pH 7.

The drawing demonstrates the effect of dilution on the initial velocity of the coupled reductase-luciferase reaction, comparing bound (Ag-L:FR) and dissolved (L+FR) forms of the enzymes. The initial maximal intensity (ordinate, $I_o$) of the coupled bioluminescence was determined at 23° C. in 1 ml of 0.02 M phosphate, pH 7, containing 0.2% BSA, 0.001% decanal, $5\times10^{-5}$ M FMN, $2.5\times10^{-4}$ M (● and ■) or $2.5\times10^{-5}$ M (o and □) NADH, and soluble luciferase plus flavin reductase (L+FR; o and ●) or the Ag-L:FR complex (□ and ■). The total amount of luciferase plus reductase was varied by dilution, so that the relative amounts of the two enzymes were constant. For samples of (L+FR), an arbitrary unit of 1 is equivalent to 0.12 mg luciferase plus 0.24 mg of flavin reductase per ml in total enzyme concentration, and $4.5\times10^{12}$ (●) or $3.4\times10^{12}$ (o) q.s$^{-1}$ in bioluminescence intensity. For samples of Ag-L:FR, an arbitrary unit of 1 is equivalent to $3.1\times10^{11}$ (■) or $1.2\times10^{11}$ (□) q.s$^{-1}$ in bioluminescence, and 50 μg immobilized luciferase plus the adsorbed flavin reductase per ml of assay solution in total enzyme concentration. The drawing shows that, for the bound enzyme system, dilution caused a proportional decrease in activity, while for the soluble system, a 10 fold dilution produced a 100 fold decrease in activity.

What is claimed is:

1. Composition comprising a single immobilized enzyme selected from the pair consisting of flavin reductase and bacterial luciferase, said enzyme being covalently bonded to a water-insoluble support and being the sole enzyme of said pair covalently bonded to said support and the other enzyme of said pair being bound to said immobilized enzyme.

2. Composition comprising a single immobilized enzyme of a pair selected from the group consisting of water-soluble glycolytic enzyme pairs, said enzyme being covalently bonded to a water-insoluble support and being the sole enzyme of said pair covalently bonded to said support and the other enzyme of said pair being bound to said immobilized enzyme.

3. The method of assaying an enzyme of a water-soluble glycolytic enzyme pair or a substrate of one of said enzymes which comprises:
   providing one enzyme of said pair immobilized on a water-insoluble support,
   bringing said immobilized enzyme into contact with a solution containing the other enzyme of said pair and the substrates of said enzymes, whereby said other enzyme is bound to said immobilized enzyme and reactions between said substrates are catalyzed by said enzymes,
   the amount of each said enzyme and each said substrate except for the enzyme or substrate to be assayed being in excess of the stoichiometric amount, and
   measuring the amount of at least one product of the last said reaction.

4. The method of assaying an enzyme of the enzyme pair consisting of bacterial luciferase and flavin reductase or a substrate of one of said enzymes which comprises:
   providing one enzyme of said pair immobilized on a water-insoluble support,
   bringing said immobilized enzyme into contact with a solution containing the other enzyme of said pair and the substrates of said enzymes, whereby said other enzyme is bound to said immobilized enzyme and reactions between said substrates are catalyzed by said enzymes,
   the amount of each said enzyme and each said substrate except for the enzyme or substrate to be assayed being in excess of the stoichiometric amount, and
   measuring the light emitted.

5. A kit for assaying a substrate for one enzyme of a water-soluble glycolytic enzyme pair comprising as components:
   (1) one enzyme only of said enzyme pair covalently bonded to a water-insoluble support and the other enzyme of said pair bound to said covalently bonded enzyme,
   (2) the substrate of said enzymes except said substrate being assayed, and
   (3) standards containing known amounts of said substrate being assayed.

6. A kit for assaying a substrate for one enzyme of the enzyme pair consisting of bacterial luciferase and flavin reductase comprising as components:
   (1) one enzyme only of said enzyme pair covalently bonded to a water-insoluble support and the other enzyme of said pair bound to said covalently bonded enzyme,
   (2) the substrates of said enzymes except said substrate being assayed, and
   (3) standards containing known amounts of said substrate being assayed.

7. In a two-enzyme system in which a reaction product of a first enzyme with first substrates serves as one of the substrates of a second enzyme, the method of assaying for the presence of any of said enzymes or substrates except for said reaction product substrate which comprises
   providing one of said enzymes immobilized by covalent bonding on a water-insoluble support,
   bringing said immobilized enzyme into contact with a solution containing the other of said enzymes and substrates of said enzymes, whereby said other enzyme is bound to said immobilized enzyme and reactions of said substrates are catalyzed by said enzymes and final products are formed, the amount of each said enzyme and each said first substrate except for the enzyme or substrate to be assayed being in excess of the stoichiometric amount, and measuring the amount of at least one final product.

* * * * *